United States Patent [19]

Reddy et al.

[11] Patent Number: 5,449,651
[45] Date of Patent: Sep. 12, 1995

[54] METALLOCENE COMPOUND FOR A CATALYST COMPONENT WITH GOOD CATALYST EFFICIENCY AFTER AGING

[75] Inventors: Baireddy R. Reddy, Baytown; Edwar S. Shamshoum, Houston, both of Tex.

[73] Assignee: Fina Technology, Inc., Dallas, Tex.

[21] Appl. No.: 196,747

[22] Filed: Feb. 14, 1994

Related U.S. Application Data

[62] Division of Ser. No. 885,104, May 18, 1992, Pat. No. 5,308,817.

[51] Int. Cl.[6] ............................................. C08F 4/64
[52] U.S. Cl. ..................................... 502/117; 502/102; 502/103; 526/160; 556/11; 556/43; 556/53
[58] Field of Search ................ 502/117, 102, 103; 556/11, 53, 43; 526/160

[56]  References Cited

U.S. PATENT DOCUMENTS 4,892,851  1/1990  Ewen et al. .......................... 556/43
5,308,817  5/1994  Reddy et al. ........................ 502/117

*Primary Examiner*—Asok Pal
*Attorney, Agent, or Firm*—M. Norwood Cheairs; Jim D. Wheelington

[57] ABSTRACT

This invention relates to a syndiospecific metallocene of a substituted iPr[(cyclopentadienyl)(fluorenyl)]zirconium dichloride containing long-chain terminal alkene, for example octenyl groups, on fluorene at C2/C7. The metallocene compound useful as a catalyst in the present invention is described by the general formula:

$$R''(C_5H_4)(C_4H_{4-m}R'_m C_5 C_4H_{4-n}R'_n)MeQ_p$$

wherein $(C_5H_4)$ is a cyclopentadienyl ring and $(C_4H_{4-m}R'_m C_5 C_4H_{4-n}R'_n)$ is a fluorenyl radical; R' is a long chain alkene substituent having 5–20 carbon atoms on the fluorene ligand at C2 or C7, each R' may be the same or different; R" is a structural bridge between the $(C_5H_4)$ and $(C_4H_{4-m}R'_m C_5 C_4H_{4-n}R'_n)$ rings to impart stereorigidity; Q is a hydrocarbon radical or a halogen; Me is a Group IIIB, IVB, VB, or VIB metal; m=0 or 1; n=1; and p is the valence of Me minus 2. Polymerizations with metallocene/MAO solutions stored at room temperature under nitrogen for several days resulted in gradual increases in polymer yields when using the metallocene of the present invention and a decrease in polymer yield when using metallocne of the prior art.

13 Claims, 5 Drawing Sheets

METALLOCENE COMPOUND FOR A CATALYST COMPONENT WITH GOOD CATALYST EFFICIENCY AFTER AGING

This is a Divisional application of application Ser. No. 07/885,104 filed on May 18, 1992 now U.S. Pat. No. 5,308,817.

BACKGROUND OF THE INVENTION

1. Field of the Invention

This invention relates to a metallocene catalyst component for olefin polymerization, specifically, to a syndiospecific metallocene catalyst component having a polymerizable functional group substituent.

2. Description of the Prior Art

German patent application 2,608,863 discloses a catalyst system for the polymerization of ethylene consisting of bis(cyclopentadienyl)-titanium dialkyl, an aluminum trialkyl and water. German patent application 2,608,933 disclosed an ethylene polymerization catalyst system consisting of zirconium metallocenes of the general formula (cyclopentadienyl)$_n$ Zr Y$_{4-n}$, wherein Y represents R$_1$CH$_2$AlR$_2$, CH$_3$CH$_2$AlR$_2$ and CH$_3$CH(AlR$_2$)$_2$ wherein R stands for an alkyl or metallo-alkyl, and n is a number within the range 1–4; and the metallocene catalyst is in combination with an aluminum trialkyl cocatalyst and water.

The use of metallocenes as catalysts in the copolymerization of ethylene and other alpha-olefins is also known in the art. U.S. Pat. No. 4,542,199 to Kaminsky, et al. disclosed a process for the polymerization of olefins and particularly for the preparation of polyethylene and copolymers of polyethylene and other alpha-olefins. The disclosed catalyst system includes a catalyst of the formula (cyclopentadienyl)$_2$MeRHal in which R is a halogen, a cyclopentadienyl or a C$_1$–C$_6$ alkyl radical, Me is a transition metal, in particular zirconium, and Hal is a halogen, in particular chlorine. The catalyst system also includes an aluminoxane having the general formula Al$_2$OR$_4$(Al(R)-O)$_n$ for a linear molecule and/or (Al(R)-O)$_{n+2}$ for a cyclic molecule in which n is a number from 4–20 and R is a methyl or ethyl moiety. A similar catalyst system is disclosed in U.S. Pat. No. 4,404,344.

U.S. Pat, No. 4,530,914 discloses a catalyst system for the polymerization of ethylene to polyethylene having a broad molecular weight distribution and especially a bimodal or multimodal molecular weight distribution. The catalyst system is comprised of at least two different metallocenes and an alumoxane. The patent discloses metallocenes that may have a bridge serving to make the rings stereorigid. The bridge is disclosed as being a C$_1$–C$_4$ alkylene radical, a dialkyl germanium or silicon, or an alkyl phosphine or amine radical.

European Patent Application 0185918 discloses a stereorigid, chiral metallocene catalyst for the polymerization of olefins. The bridge between the cyclopentadienyl groups is disclosed as being a linear hydrocarbon with 1–4 carbon atoms or a cyclical hydrocarbon with 3–6 carbon atoms. The application discloses zirconium as the transition metal used in the catalyst, and linear or cyclic alumoxane is used as a co-catalyst. It is disclosed that the system produces a polymer product with a high isotactic index.

Catalysts that produce isotactic polyolefins are disclosed in U.S. patent application Ser. No. 317,089 filed Feb. 28, 1989, and U.S. Pat, Nos. 4,794,096 and 4,975,403. This application and these patents disclosed chiral, stereorigid metallocene catalyst components that are used in the polymerization of olefins to form isotactic polymers and are especially useful in the preparation of a highly isotactic polypropylene.

Catalysts that produce syndiotactic polyolefins are disclosed in U.S. Pat. No. 4,892,851. Many metallocenes consisting of deliberate structural modifications to a syndiospecific catalyst, namely, iPr[(cyclopentadienyl)(fluorenyl)]zirconium dichloride, as disclosed in U.S. Pat. No. 4,892,851 (hereinafter referred to as iPr[Cp(Flu)ZrCl$_2$]). The structural modifications have been correlated with polymer properties. Some of the polymer properties which can be very effectively controlled by catalyst structure modifications include molecular weight, melting point and the microstructure. However, all the modifications to the iPr[Cp(Flu)]ZrCl$_2$ have resulted in a decrease in the catalyst efficiency compared to the unsubstituted complex under any given set of polymerization conditions. So far, there have not been any efforts made to use substituent effects for manipulating polymerization efficiencies of the metallocenes.

Patent application Ser. No. 07/888,192 now U.S. Pat. No. 5,393,851 shows that MAO solutions of iPr[Cp(Flu)]ZrCl$_2$ are stable at room temperature for at least two weeks losing initially only about 20% efficiency. This loss in catalyst efficiency can be reduced by storing the solutions at a lower temperature (for example at −3° C.).

SUMMARY OF THE INVENTION

A syndiospecific metallocene of a substituted iPr[(cyclopentadienyl)(fluorenyl)]zirconium dichloride containing long-chain terminal alkene (hereinafter referred to as "diolefin catalyst"), for example octenyl groups, on fluorene at C2/C7 was synthesized. The alkene functionality can, in principle, be self-polymerized by the catalyst in presence of cocatalysts such as MAO or ion-pair systems, or it can be co-polymerized with propylene thus supporting the catalyst in a polypropylene matrix.

The metallocene compound useful as a catalyst in the present invention is described by the general formula:

wherein (C$_5$H$_4$) is a cyclopentadienyl ring and (C$_4$H$_{4-m}$R'$_m$C$_5$C$_4$H$_{4-n}$R'$_n$) is a fluorenyl radical; R' is a long chain alkene substituent having 5–20 carbon atoms on the fluorene ligand at C2 or C7, each R' may be the same or different; R" is a structural bridge between the (C$_5$H$_4$) and (C$_4$H$_{4-m}$R'$_m$C$_5$C$_4$H$_{4-n}$R'$_n$) rings to impart stereorigidity; Q is a hydrocarbon radical or a halogen; Me is a Group IIIB, IVB, VB, or VIB metal; m=0 or 1; n=1; and p is the valence of Me minus 2.

BRIEF DESCRIPTION OF THE DRAWINGS

A more complete appreciation of the invention and many of the attendant advantages thereof will be readily understood by reference to the following detailed description when considered in connection with the accompanying drawings in which like numerals in different figures represent the same structures or elements wherein.

DETAILED DESCRIPTION OF THE INVENTION

The syndiospecific catalyst iPr[Cp(Flu)]ZrCl$_2$ is disclosed in U.S. Pat. No. 4,892,851. Introduction of long chain olefin-terminated alkyl groups at C2 and C7 of fluorene in iPr[Cp(Flu)]ZrCl$_2$ retains the syndiospecificity of the metallocene. However, the new catalyst is less active and less stereospecific than iPr[Cp(Flu)]ZrCl$_2$ and gives polymer of lower molecular weight. This may be in part due to the coordination of side chain carbon-carbon double bonds to zirconium thus competing for coordination with propylene. Also contributing to the decreased catalyst efficiency is the general effect of any substituent at these positions as disclosed in patent application Ser. No. 07/903,058.

The metallocene compounds useful in the present invention is described by the general formula:

wherein (C$_5$H$_4$) is a cyclopentadienyl ring and (C$_4$H$_{4-m}$R'$_m$C$_5$C$_4$H$_{4-n}$R'$_n$) is a fluorenyl radical; R' is a long chain alkene substituent having 5-20 carbon atoms on the fluorene ligand at C2 or C7, each R' may be the same or different; R" is a structural bridge between the (C$_5$H$_4$) and (C$_4$H$_{4-m}$R'$_m$C$_5$C$_4$H$_{4-n}$R'$_n$) rings to impart stereorigidity; Q is a hydrocarbon radical or a halogen; Me is a Group IIIB, IVB, VB, or VIB metal; m=0 or 1; n=1; and p is the valence of Me minus 2. Preferably, R' is the same. Preferably, R' is a long chain alkene substituent having 6-10 carbon atoms on the fluorene ligand at C2 or C7, and, more preferably is octenyl. Preferably, Me is a Group IVB metal, more preferably is titanium, zirconium or hafnium and, most preferably is zirconium. Preferably, Q is chlorine. Preferably, R" is selected from the group consisting of a substituted or unsubstituted alkyl radical having 1-4 carbon atoms as the bridging component and substituents of hydrocarbyl radicals having 1-10 carbon atoms or a compound containing silicon, germanium, phosphorus, nitrogen, boron or aluminum as the bridging component and substituents of hydrocarbyl radicals having 1-10 carbon atoms, more preferably, a methylene, ethylene, isopropyl, diphenylmethyl or dimethylsilyl radical and, most preferably, an isopropyl radical. This isopropyl radical is also described as a dimethyl-substituted methyl radical, having one carbon as the bridging component and two methyl substituents. A specific example of the metallocene compound useful in the present invention is iPr(Cp)(2,7-di-1-octen-8-ylfluorenyl)ZrCl$_2$.

A catalyst system using the metallocene compound disclosed above can be formed with a cocatalyst. The preferred cocatalyst is an organoaluminum compound of the general formula (R-Al-O) in the cyclic form and R(R-Al-O)$_n$AlR$_2$ in the linear form wherein R is an alkyl group with 1-5 carbons and n is an integer from about 1 to about 20. Preferably, the organoaluminum compound is an aluminoxane and, more preferably, is methylalumoxane.

The most significant feature of the diolefin catalyst is the effect of its aging process with aluminoxane solutions on the polymerization yields and polymer properties. The polymer yields were more than doubled by the aging process. Accompanying the increased polymer yields are increased polymer molecular weight, melting point and bulk density. These observations suggest that the catalysts containing polymerizable olefinic groups represent new class of syndiospecific metallocenes.

The invention having been generally described, the following examples are given as particular embodiments of the invention and to demonstrate the practice and advantages thereof. It is understood that the examples are given by way of illustration and are not intended to limit the specification or the claims to follow in any manner.

Figure 1:
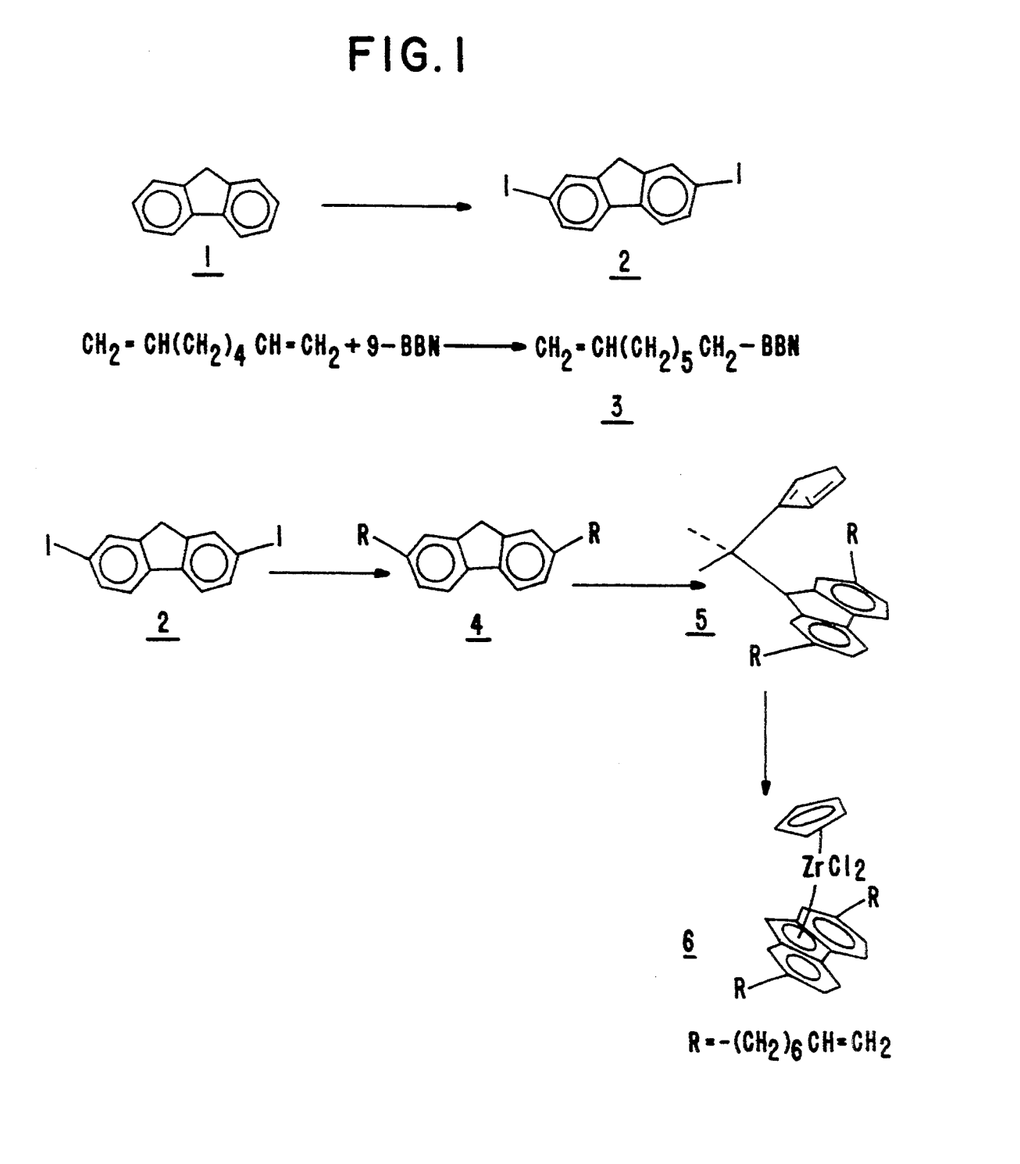
FIG. 1 is a synthesis scheme for producing iPr[(cyclopentadienyl)(fluorenyl)]zirconium dichloride type containing long chain alkene substituents on the fluorenyl ring.

The catalyst synthesis was achieved in a multi-step synthesis as described below in FIG. 1.

i. synthesis of 2,7-diiodofluorene (2)
ii. synthesis of 1-octenyl-8-BBN (3)
iii. synthesis of 2,7-di-1-octen-8-ylfluorene (4)
iv. synthesis of isopropyl(cyclopentadienyl) (2,7-di-1-octen-8-ylfluorene)(5)
v. synthesis of iPr(cyclopentadienyl) (2,7-di-1-octen-8-ylfluorene) zirconium dichloride (6)

i. Synthesis of 2,7-diiodofluorene (2)

Figure 2:
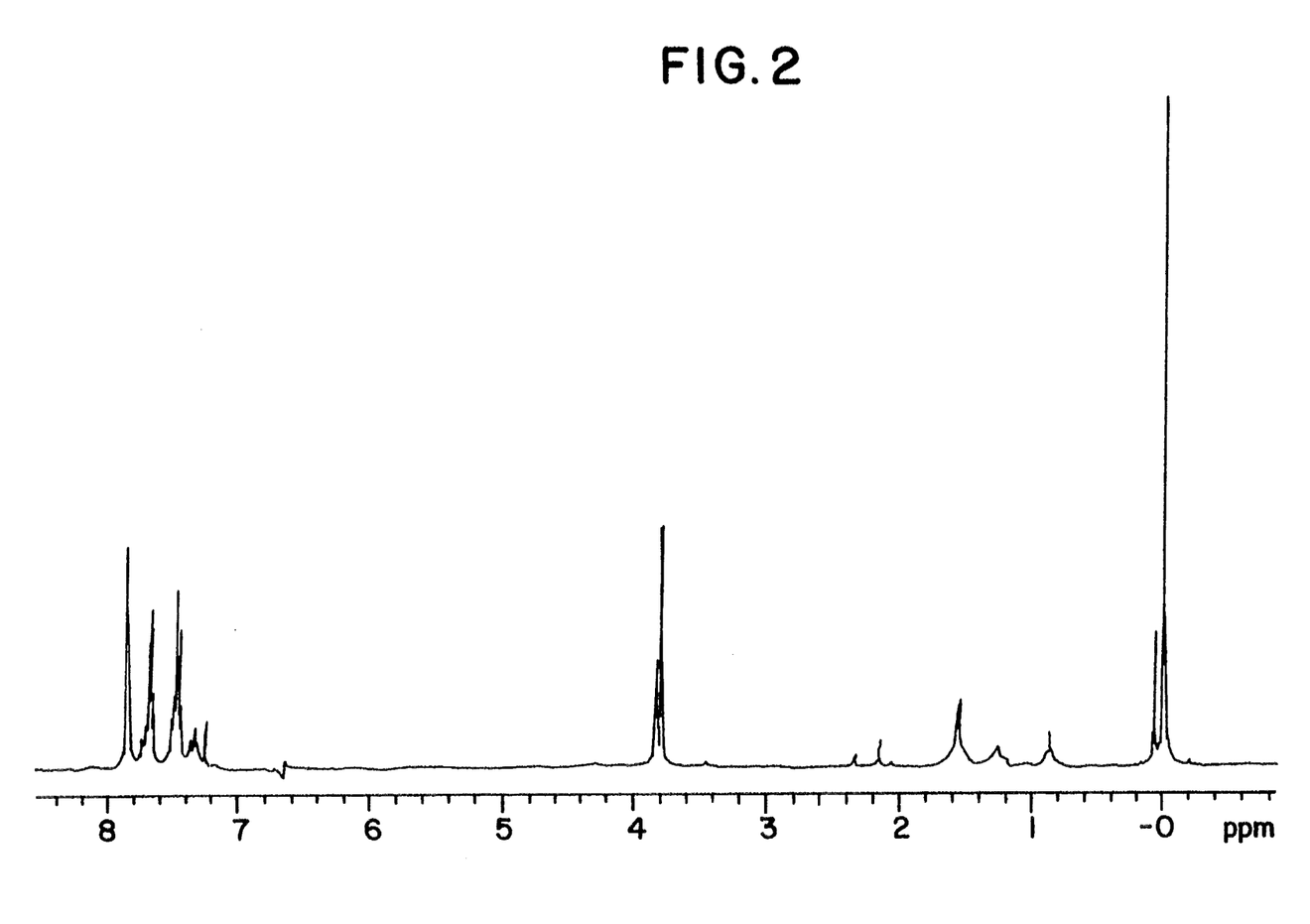
FIG. 2 is the proton NMR spectrum of 2,7-diiodofluorene.

The procedure disclosed in Ogata, y., Urasaki, I.J. Chem. Soc 1970, 12 1689, 1691 was used to prepare 2,7-diiodofluorene from fluorene and iodine. To a stirred solution of fluorene (5.0 g, 0.03 mol) and iodine (9.1 g, 0.036 mol) in 180 ml acetic acid was added at 50° C. dropwise peracetic acid (4.7M, 5.1 ml, 0.03 mol) over 6 hours. Precipitation of off-white solid occurred three hours after the addition of peroxide was started. The reaction mixture was allowed to cool down with icebath and the solid was filtered. The solid was washed with a solution of potassium iodide and sodium bisulfite, followed by water. The proton NMR spectrum (FIG. 2) agrees well with the expected structure.

ii. Synthesis of 1-octenyl-9-BBN (3)

The procedure disclosed in Chung, T. C. et al. Macromolecules, 1988, 21, 865 was used to prepare the title compound from 1,7-octadiene and 9-BBN. A 500 ml round bottom flask equipped with addition funnel was charged with 60 ml 1,7-octadiene. A solution of 9-BBN dimer (100 mmol) in 200 ml anhydrous tetrahydrofuran (THF) was added dropwise at room temperature and stirred overnight. The solvent and excess diene were removed by distillation at 60°-70° C. and 10 mtorr. The remaining liquid was distilled at 120°-140° C. and 10 mtorr. The yield was 18.8 g. The liquid is an air-sensitive, and pyrophoric material.

iii. Synthesis of 2,7-di-(1-octen-8-yl)fluorene (4)

The general procedure described in Suzuki, A., et al J. Am. Chem. Soc. 1989, 111, 314 for coupling of aryl iodides with B-alkyl-9-borabicyclononane derivatives using organopalladium catalyst was followed.

Figure 3:
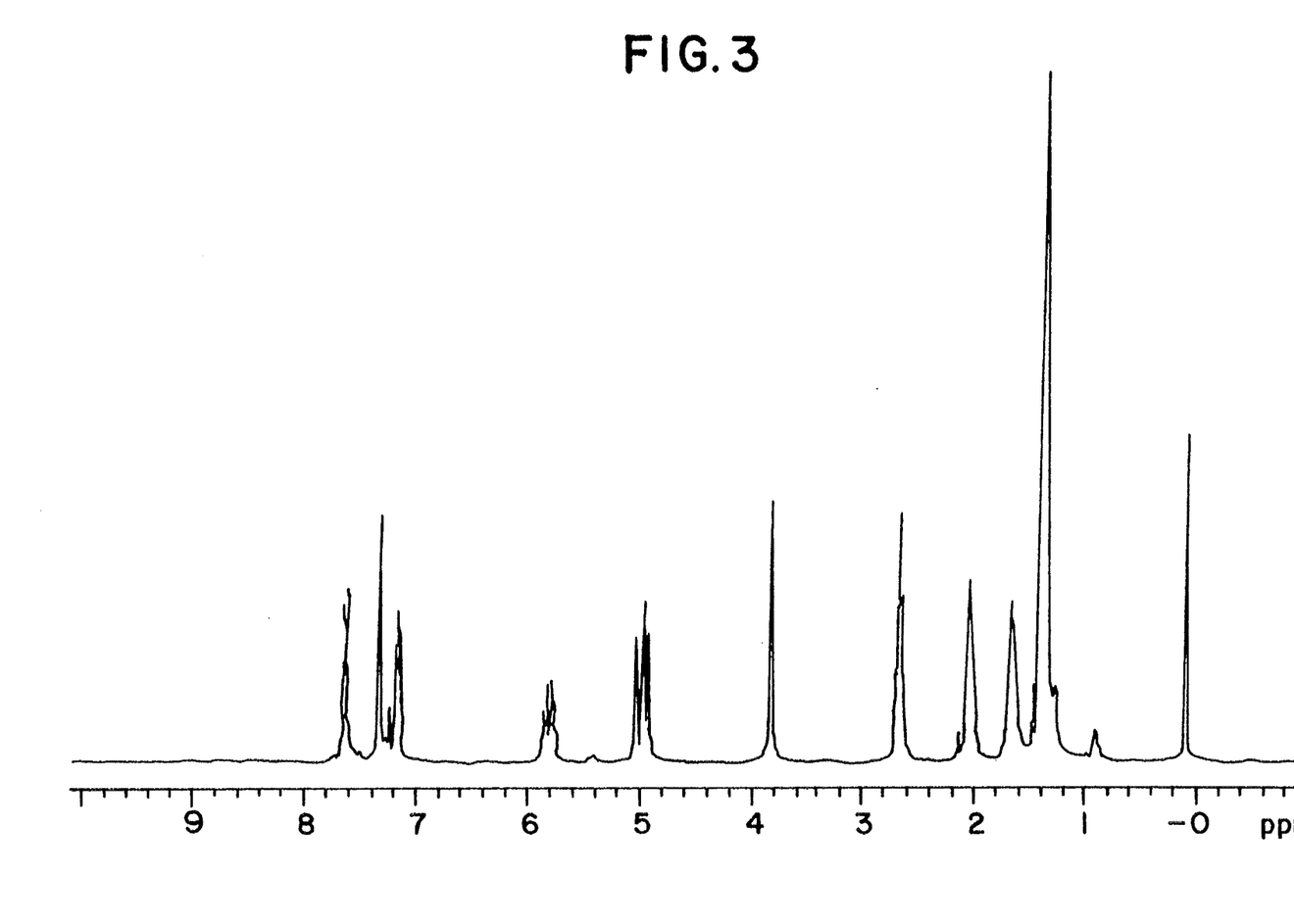
FIG. 3 is the proton NMR spectrum of 2,7-di-1-octen-8-yl fluorene.

To a suspension of 5.0 g (0.012 mol) of diiodofluorene (1), 0.25 g bis(triphenylphosphine) palladium dichloride, 6.60 g potassium carbonate in 300 ml anhydrous DMF, was added a THF (3 ml) solution of 1-octene-8-BBN (2) under argon. The mixture was heated to 50° C.

overnight. The solvents were removed by vacuum distillation. The residue was extracted with hexane and the extracts were passed through a short bed of neutral alumina and eluted with hexane. Removal of hexane yielded 4 as a white solid. The product was characterized by proton NMR (FIG. 3).

iv. Synthesis of iPr(2,7-dioctenylfluorenyl) (Cp) (5)

Figure 4:
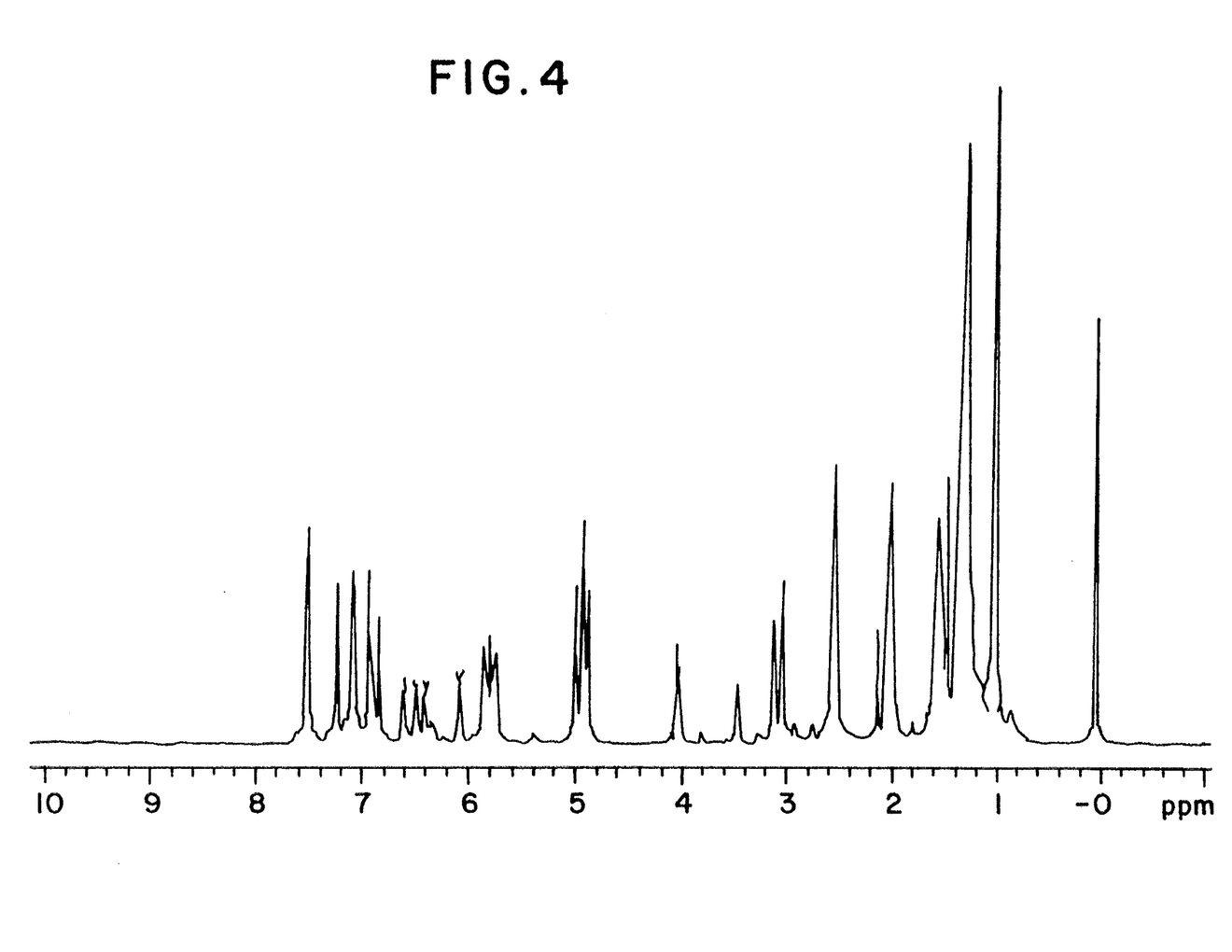
FIG. 4 is the proton NMR spectrum of iPr(cyclopentadienyl) (2,7-di-1-octen-8-yl fluorene).

To a solution of dioctenylfluorene 3 (2.0 g, 5.2 mmol) in dry ether (100 ml) kept at 0° C., a 1.4M solution of methyllithium in ether was added and stirred overnight at room temperature. The resulting yellow solution was cooled to −50° C. and a solution of 6,6-dimethylfulvene (0.82 ml, 6.8 mmol) in dry THF was added dropwise; the reaction mixture allowed to warm to room temperature and stirred overnight. Additional amount of THF (20 ml) was added and the reaction mixture was concentrated by passing a gentle stream of argon for 18 hours. The solvents were removed under vacuum and a mixture of hexane and dilute hydrochloric acid were added. The layers were separated and the aqueous layer was extracted twice with ether. The combined organic layers were washed with water followed by saturated sodium chloride solution and dried over anhydrous MgSO₄. The solvents were removed in vacuo; the resulting oil was successively chromatographed on neutral alumina and silica gel and eluted with 1:1 mixture of methylene chloride and hexane to obtain the ligand as an orange oil. Proton NMR spectrum (FIG. 4) confirmed the expected structures for the isomeric ligand mixture.

v. Synthesis of iPr(2,7-di-1-octen-8-ylfluorenyl) (Cp) ZrCl₂ (6)

Figure 5:
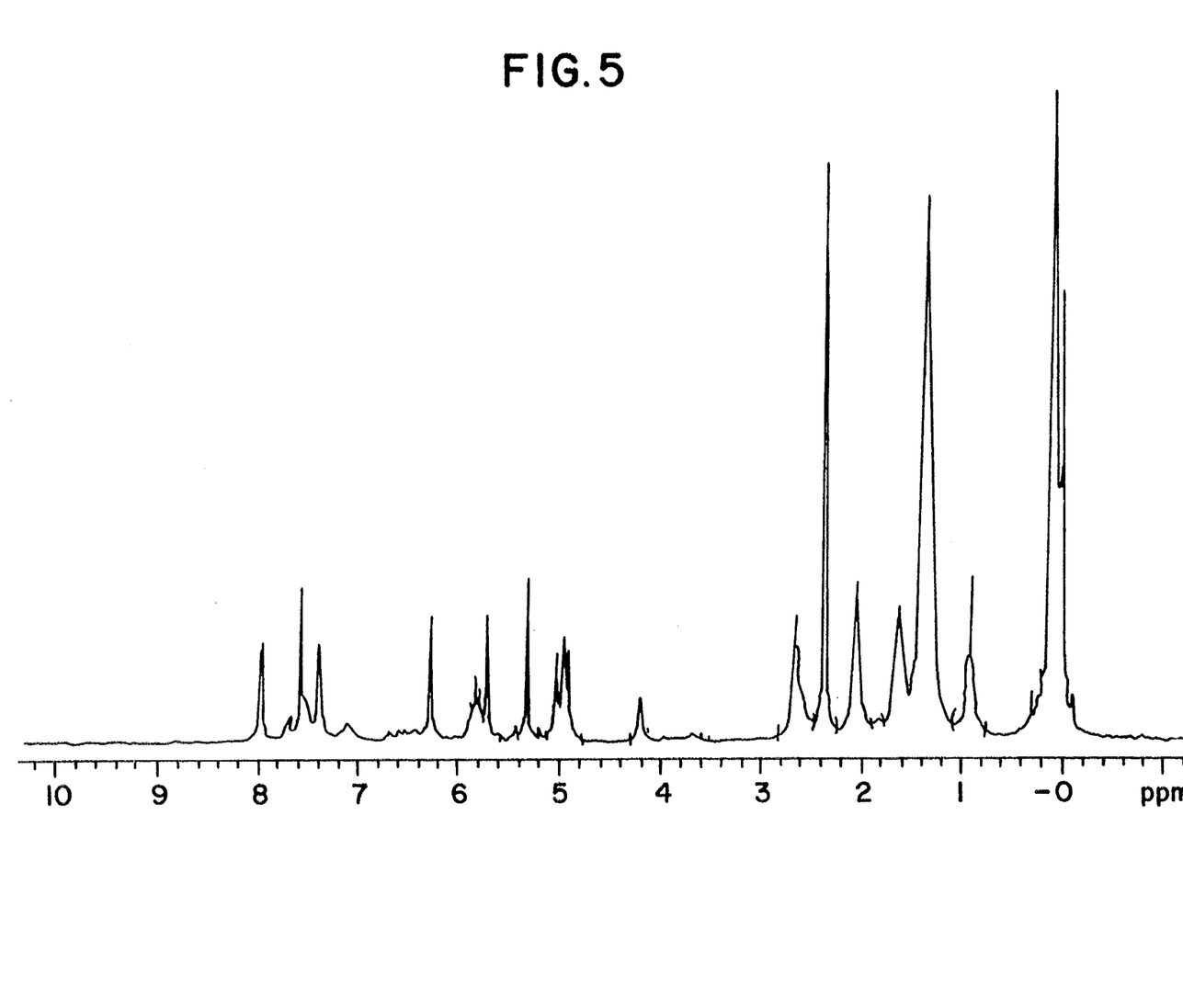
FIG. 5 is the proton NMR spectrum of iPr(cyclopentadienyl) (2,7-di-octen-8-ylfluorenyl)zirconium dichloride.

To a solution of 1.2 g of the ligand 4 in anhydrous THF (50 ml), a 1.4M solution of methyllithium in ether (3.6 ml) was added and stirred overnight. The solvents were removed from the dark red solution under high vacuum to obtain a dark red oil. The flask was cooled to −78° C., and methylene chloride prechilled to −78° C. was cannulated in and stirred. A slurry of ZrCl₄ (0.5 g, 2.1 mmol) in methylene chloride prechilled to −78° C. was cannulated into the dianion solution. The temperature was allowed to slowly warm up to room temperature and stirring was continued to 3 hours. The methylene chloride was removed under high vacuum, the solid was taken into the drybox and recrystallized in small batches. The crude product was washed with hexane; the hexane layers discarded. The hexane insoluble solid was dissolved in dry methylene chloride and filtered. The solvent was removed under high vacuum, to obtain 5 as an orange solid which was essentially pure as judged by proton NMR (FIG. 5).

PROCEDURES FOR AGING CATALYST/ALUMOXANE SOLUTIONS

Method A

A weighed amount of the catalyst was dissolved in less than required amount of Texas Alkyls MAO (in heptane) or Schering MAO (in toluene) and the solution was kept in a Wheaton bottle wrapped in aluminum foil and stored inside the drybox either at room temperature or at 0° C. An aliquot was taken at regular intervals; diluted with additional amount alumoxane and the polymerization was run.

Method B

A weighed amount of the catalyst was dissolved in required amount of alumoxane and stored in the drybox at specified temperature away from light. A 5 ml aliquot was taken at regular intervals and polymerizations were run.

Method C

A weighed amount of the catalyst was dissolved in MMAO (Texas Alkyls) and heated to 50° C. for one hour under nitrogen and the polymerization was run.

POLYMERIZATIONS

All the polymerizations were run in bulk propylene (1.4 L) in a magnedrive, packless Zipperclave reactor. The catalyst/alumoxane solution taken in a stainless steel sample cylinder was charged along with 400 ml propylene into the reactor containing 1 liter propylene at room temperature. Stirring at 1200 rpm was started and the temperature was raised to 60° C. within 5 minutes. The stirring was decreased to 300 rpm and the polymerization was run for one hour. The temperature of the reactor was lowered to room temperature. The monomer was vented, the reactor was opened and polymer fluff was collected. Any polymer ring around and stirrer and baffles was collected separately and weighed. The polymer which stuck to the reactor walls and the stirrer was extracted with toluene at 90° C. and precipitated by the addition of methanol. The precipitated polymer was filtered, dried and weighed. The sum of the polymer obtained from the ring and toluene extraction was defined as fouling.

TABLE 1

Comparison of Polymerization Data Obtained with the Diolefin Catalyst Using Texas Alkyls MMAO or Schering MAO Under Standard Conditions

| Example | Catalyst(mg)/ Alumoxane(ml) | Poly. T C. | Total yield(g) | Effic- g/g-h | Melt pt °C. | Mw/1000 (gpc) | MWD | BD g/cc | % Fouling |
|---|---|---|---|---|---|---|---|---|---|
| 1 | 2.0/5.0 | 60 | 26 | 13000 | 126 | 57.1 | 2.4 | 0.17 | 46 |
|   | MAO | 60 | 29 | 14500 | 128 | — | — | 0.24 | 48 |
| 2 | 2.0/5.0 |  |  |  |  |  |  |  |  |
|   | MAO |  |  |  |  |  |  |  |  |
| 3 | 2.0/5.0 | 30 | 6 | 3000 | 134 | 97.2 | 2.8 | <0.10 | <5 |
|   | MAO |  |  |  |  |  |  |  |  |
| 4 | 2.0/5.0 | 60 | 72 | 36000 | 126 | 56.3 | 2.3 | 0.22 | 32 |
|   | MMAO |  |  |  |  |  |  |  |  |

TABLE 2

Polymerization Data With MAO Solutions of The Diolefin Catalyst Aged[1] at Room Temperature

| Example | Catalyst(mg)/ MAO (ml) | Age (hr) | Poly. wt(g) | Effic. g/g-h | % Effic increase | DSC °C. | Mw/1000 (gpc) | MWD | BD g/ml | % Fouling[4] |
|---|---|---|---|---|---|---|---|---|---|---|
| 5 | 2.0/5.0 | 0 | 26 | 13000 | — | 126 | 57.1 | 2.4 | 0.16 | 52 |
| 6 | 2.0/5.0 | 24 | 45 | 22500 | 72 | 129 | 68.6 | 2.6 | 0.27 | 42 |
| 7 | 2.0/5.0 | 48[2] | 80 | 40000 | 210 | 130 | 113.5 | 3.2 | 0.29 | 90 |
| 8 | 2.0/5.0 | 72 | 58 | 29000 | 120 | 130 | 70.5 | 2.8 | 0.26 | 91 |
| 9 | 2.0/5.0 | 96[3] | 37 | 18500 | 42 | 130 | 72.5 | 2.5 | n.d.[5] | 100 |

1. A stock solution of the catalyst was made in Schering MAO in a Wheaton bottle, wrapped in aluminum foil and stored at room temperature inside the dry box.
2. The original purple color of the stock solution changed to red purple.
3. The stock solution color changed to brown.
4. Fouling was calculated by adding the weight of the ring and weight of toluene extract and dividing the sum by the total yield.
5. n.d - not determined.

TABLE 3

Bulk Polymerization Data with Schering MAO Solutions of the Diolefin Catalyst Aged at 0° C.

| Run # | Catalyst(mg)/ MAO(ml) | Age Period(h) | Poly. wt(g) | Effic. g/g-h | DSC °C | Mw/1000 (gpc) | MWD | % Fouling[1] |
|---|---|---|---|---|---|---|---|---|
| 10 | 2.0/5.0 | 24 | 23 | 11500 | 128 | 54.6 | 3.7 | 91 |
| 11 | 2.0/5.0 | 48 | 19 | 9500 | 129 | 56.4 | 4.0 | 100 |
| 12 | 2.0/5.0 | 72 | 10 | 5000 | 128 | n.d | n.d | 100 |

1. Fouling was calculated by adding the weight of the ring and weight of Toluene extract and dividing the sum by the total yield.

TABLE 4

Bulk Polymerization Data with Texas Alkyls MMAO Solutions of the Diolefin Catalyst Aged at Room Temperature and at 50° C.

| Run # | Cat.(mg) MMAO (ml) | Age Time(h) | Aging Temp(C.) | Poly. wt(g) | Effic. g/g-h | DSC (°C.) | Mw/1000 (gpc) | MWD | B.D g/cc |
|---|---|---|---|---|---|---|---|---|---|
| 13 | 2.0/5.0 | 0 | 24 | 72 | 36000 | 126 | 56 | 2.3 | 0.22 |
| 14 | 2.0/5.0 | 24[1] | 24 | 104 | 52000 | 129 | 67 | 2.7 | n.d |
| 15 | 1.0/5.0[2] | 24 | 24 | 87 | 87000 | 129 | 75 | 2.8 | n.d |
| 16 | 1.6/5.0[3] | 1 | 50 | 61 | 38000 | 128 | 77 | 2.7 | n.d |

1. The original light purple solution of the MMAO solution of the catalyst turned to golden brown in 24 hours.
2. 3.0 mg of the catalyst was dissolved in 5 ml Texas Alkyls MMAO; aged for 24 hours; an aliquot of 1.6 ml (approx. 1 mg catalyst) was taken and diluted with 3.4 ml MMAO and the polymerization was run.
3. A solution of the catalyst (1.6 mg) and MMAO (5 ml) was heated for one hour at 50° C. in a Wheaton bottle, cooled and injected into the reactor.

TABLE 5

Bulk Polymerization Data with MAO Solutions if iPr(Flu-Cp)ZrCl2 aged at room temperature

| Compare Example | Catalyst(mg)/ MAO(ml) | Age time(hr) | Poly. wt(g) | Effic. g/g-h | DSC °C. | Mw/1000 (gpc) | MWD | BD g/cc | % Fouling |
|---|---|---|---|---|---|---|---|---|---|
| 1 | 0.50/5.0 | 0 | 145 | 290000 | 136 | 85.0 | 2.5 | 0.17 | 7.4 |
| 2 | 0.5/5.0 | 24 | 155 | 310000 | 138 | 87.6 | 2.6 | 0.16 | 20.0 |
| 3 | 0.5/5.0 | 48 | 104 | 208000 | 138 | 89.5 | 2.4 | 0.18 | 39.0 |
| 4 | 0.5/5.0 | 72 | 113 | 226000 | 137 | 87.6 | 2.4 | 0.21 | 38.0 |

All the runs except Comparative Example 4 were run from the same batch of stock solution of iPr(Cp-Flu)ZrCl2. The 72 hour polymerization (Comparative Example 4) was run with a solution made and aged separately.

TABLE 6

Bulk Polymerization Data with MAO Solutions if iPr(Flu-Cp)ZrCl2 Aged at 0° C.

| Compare Example | Catalyst(mg) MAO (ml) | Age time(h) | Poly. wt(g) | Effic. g/g-h | DSC °C. | Mw/1000 (gpc) | MWD | BD g/cc | % Fouling |
|---|---|---|---|---|---|---|---|---|---|
| 5 | 0.5/5.0 | 0 | 145 | 290000 | 136 | 85.4 | 2.5 | 0.17 | 7 |
| 6 | 0.5/5.0 | 24 | 137 | 274000 | 137 | 89.6 | 2.4 | 0.16 | 30 |
| 7 | 0.5/5.0 | 48 | 109 | 218000 | 137 | 89.6 | 2.4 | 0.17 | 35 |
| 8 | 0.5/5.0 | 72 | 129 | 258000 | 136 | 88.4 | 2.5 | 0.15 | 29 |

All polymerizations except Comparative Example 8 were run from the same stock solution. MAO/catalyst solution for Comparative Example 8 was made separately and aged for 72 hours.

Comparison of polymerization data obtained with iPr[Cp(Flu)]ZrCl$_2$ and the diolefin catalyst at 60° C. (Table 1) indicates that the diolefin catalyst is less efficient and less stereospecific than iPr[Cp(Flu)]ZrCl$_2$. All the results from the aging studies point to the conclusion that the new catalyst is self-polymerizing in the presence of MAO. Aged diolefin catalyst/MAO solution increased the bulk density of the polymer but the reactor fouling remained high.

Much of the polymerization work with the diolefin catalyst was concerned with the reactivity of the olefin groups on the side chains under the polymerization conditions. Polymerizations with catalyst/MAO stock solutions stored at room temperature under nitrogen for several days resulted in gradual increases in polymer yields over a three day period and then gradually the yields decreased (Table 2). In parallel with increase in polymer yields with aging of MAO/catalyst solutions, there was a simultaneous increase in polymer molecular weight, molecular weight distribution, melting point and bulk density. After prolonged period of aging (>48 h), a decrease in these polymer property values with the exception of melting point occurred simultaneously with a decrease in polymer yields. The decrease in polymer yield with prolonged aging appears to be due to catalyst decomposition as evidenced by change in the purple color of the catalyst/MAO solutions to brown accompanied by deposition of insoluble solids.

The aging temperature also had significant effect on polymerization behavior of the diolefin catalyst. When the aging temperature was 0° C., the polymer yields dropped gradually with no significant changes in polymer properties (Table 3). The color of the catalyst/MAO solution changes from purple to pink during the aging period, indicating structural changes. The difference in efficiencies of the catalyst systems aged at room temperature and at 0° C. suggest that the chemical reactions, possibly polymerization, undergone by the olefin functional groups on the side chains at room temperature do not take place at 0° C.

The polymerization studies with the diolefin catalyst/MMAO in addition to room temperature aging, elevated temperature (50° C.) aging also (Table 4). Better polymer yields were obtained with Texas alkyls MMAO than with Schering MAO. Interestingly, the purple color of the catalyst/MMAO solution turned to yellow after storing the solution at room temperature for 24 hours. Heating the diolefin catalyst/MMAO solution for one hour under nitrogen, changed the color from purple to yellow. The polymer yield did not decrease because of the heating. The significance of the color changes with MMAO is not clear.

Results obtained from the aging studies with iPr[Cp(Flu)]ZrCl$_2$/(M)MAO solutions (Tables 5-6) present interesting comparison with the above results and serve to show that the diolefin catalyst belongs to a class of metallocenes different from iPr[Cp(Flu)]ZrCl$_2$.

The changes in catalyst activity with aging can be rationalized in terms of in situ polymerization of the olefin groups by the active form of the metallocene in MAO. This phenomenon could be initiated either intermolecularly or intramolecularly. As is true with metallocene catalyzed alpha-olefin polymerizations, the rate of polymerization is greater at elevated temperature. This would explain the differences in polymerization efficiencies with MAO solutions of diolefin catalyst aged at room temperature and at 0° C.

The gradual increase in catalytic activity over a period of several days is consistent with slow rate of polymerization of alpha-olefins larger than propylene by metallocenes such as iPr[Cp(Flu)]ZrCl$_2$. It is quite likely that the side chain olefin groups in the cationic metallocene (produced immediately after dissolving the dichloride complex in MAO) are pi-complexed to the zirconium either intra- or inter-molecularly. Such internal complexation of olefins to the active metal center makes the metal center less available to propylene coordination, thus decreasing catalyst efficiency. Such internal coordination may also play a role in decreasing the polymer molecular weight and melting point. Removal of such internal coordination by polymerizing the side chain olefins provides for efficient and free access of propylene to zirconium.

The proposed polymeric catalyst system is expected to be heterogeneous in composition because of different ways the two internal olefins can be polymerized with other catalyst units. The heterogeneous nature of the polymerized catalyst is likely to be responsible for the increase in MWD and also increased bulk density of the polymer obtained with the catalyst solutions aged for 48 hours.

Initial polymerization results with catalyst samples containing lithium chloride when compared with the catalyst samples not containing lithium chloride suggested that presence of lithium chloride actually increased the polymer yield slightly. This was confirmed by performing polymerizations with samples containing lithium chloride (558-64, Table 8) from the catalyst preparation and comparing the results with the same batch of the catalyst sample from which the lithium chloride was removed (558-65) by filtration of methylene chloride solution of the same sample. Addition of more lithium chloride to the catalyst sample already containing lithium chloride from preparation did not change the polymer yield significantly. Aging of MAO solutions of catalyst samples containing large amounts of lithium chloride also did not change the polymer yields significantly. It appears that lithium chloride when present in small quantities enhances polymer yields.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letter of patent of the United States is:

1. A metallocene compound described by the general formula:

wherein ($C_5H_4$) is a cyclopentadienyl ring and ($C_4H_{4-m}R'_mC_5C_4H_{4-n}R'_n$) is a fluorenyl radical; R' is a long chaing alkene substituent on the fluorene ligand at C2 or C7, each R' may be the same or different; R" is a structural bridge between the ($C_5H_4$) and ($C_4H_{4-m}R'_mC_5C_4H_{4-n}R'_n$) rings to impart stereorigidity; Q is a hydrocarbon radical or a halogen; Me is a Group IIIB, IVB, VB, or VIB metal; $1 \leq m \leq 4$; $0 \leq n \leq 4$; and p is the valence of Me minus 2.

2. A metallocene compound as recited in claim 1 wherein R' is at both C2 and C7.

3. A metallocene compound as recited in claim 2 wherein R' is the same.

4. A metallocene compound as recited in claim 1 wherein R' is a long chain alkene substituent having 6-10 carbon atoms.

5. A metallocene compound as recited in claim 1 wherein R' is octenyl.

6. A metallocene compound as recited in claim 1 wherein the metallocene compound is iPr(2,7-di-1-octen-8-ylfluorenyl) (Cp) ZrCl$_2$.

7. A metallocene compound as recited in claim 1 wherein Me is a Group IVB metal.

8. A metallocene compound as recited in claim 1 wherein Me selected from the group consisting of titainium, zirconium and hafnium.

9. A metallocene compound as recited in claim 1 wherein Me is zirconium.

10. A metallocene compound as recited in claim 1 wherein Q is chlorine.

11. A metallocene compound as recited in claim 1 wherein R″ is selected from the the group consisting of a substituted or unsubstituted alkyl radical having 1–4 carbon atoms as the bridging component and substituents of hydrocarbyl radicals having 1–10 carbon atoms or a compound containing silicon, germanium, phosphorus, nitrogen, boron or aluminum as the bridging component and substituents of hydrocarbyl radicals having 1–10 carbon atoms.

12. A metallocene compound as recited in claim 1 wherein R″ is a selected from the group consisting of a methylene, ethylene isopropyl, diphenylmethyl or dimethylsilyl radical.

13. A metallocene compound as recited in claim 1 wherein R″ is an isopropyl radical.

* * * * *